United States Patent [19]

Kambour

[11] Patent Number: 5,122,556
[45] Date of Patent: Jun. 16, 1992

[54] TETRA (LOWER ALKARYL) P-PHENYLENE DIPHOSPHATE-POLYCARBONATE BLENDS

[75] Inventor: Roger P. Kambour, Schenectady, N.Y.

[73] Assignee: General Electric Company, Schenectady, N.Y.

[21] Appl. No.: 513,419

[22] Filed: Apr. 23, 1990

[51] Int. Cl.$^5$ ............................................. C08K 5/523
[52] U.S. Cl. ..................................... 524/141; 524/611
[58] Field of Search ....................... 524/127, 611, 141; 558/162

[56] References Cited

U.S. PATENT DOCUMENTS

| | | | |
|---|---|---|---|
| 2,520,090 | 8/1950 | Barrett | 558/162 |
| 3,639,506 | 2/1972 | Haat | 524/141 |
| 4,078,016 | 3/1978 | Kramer | 524/126 |
| 4,463,130 | 7/1984 | Serini et al. | 525/67 |
| 4,766,165 | 8/1988 | Kress | 525/68 |

FOREIGN PATENT DOCUMENTS

| | | |
|---|---|---|
| 1261500 | 9/1989 | Canada . |
| 01033230 | 3/1984 | European Pat. Off. . |
| 0174493 | 3/1986 | European Pat. Off. . |
| 0206058 | 12/1986 | European Pat. Off. . |
| 363608 | 4/1990 | European Pat. Off. . |
| 59-45341 | 3/1984 | Japan . |
| 59-202240 | 11/1984 | Japan . |

OTHER PUBLICATIONS

Robert W. Stackman "Phosphorus Based Additives . . . Esters" Ind. Evp. Chem. Prod. Res. Dev. vol. 21, No. 2, 1982 pp. 332-336.

Primary Examiner—Veronica P. Hoke
Attorney, Agent, or Firm—William H. Pittman; James C. Davis, Jr.

[57] ABSTRACT

A polycarbonate-di(alkaryl) p-phenylene diphosphate plasticizer matrix has a tensile strength and elastic modulus higher than neat polycarbonate. By blending an impact modifier with the matrix, resin blends having a wide variety of impact and tensile properties are prepared. The matrix can be used for thin wall instrument housings which can be injection molded to close tolerance. The di(alkaryl) p-phenylene diphosphate has the formula

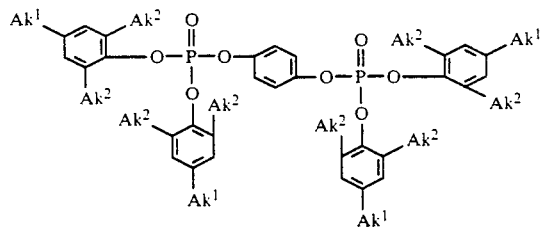

wherein
each $Ak^1$ is independently hydrogen or a methyl radical and each $Ak^2$ is independently a monovalent hydrocarbon radical having from one to four carbon atoms.

13 Claims, No Drawings

TETRA (LOWER ALKARYL) P-PHENYLENE DIPHOSPHATE-POLYCARBONATE BLENDS

This invention relates to blends of tetra(lower alkaryl) p-phenylene diphosphates with polycarbonates and optionally with impact modifiers.

The superior physical properties of polycarbonates render them useful in many application areas. However polycarbonates are deficient for some applications in certain properties such as stiffness, strength, fire resistance, and melt flow properties. Therefore there is considerable activity in the development of blends of polycarbonates with impact modifiers, flame retardants and plasticizers or flow modifiers.

The blends thus prepared are, however, often deficient because the addition of one material to improve one property is usually at the expense of a second beneficial property inherent in the polycarbonate. Thus, many blends of polycarbonates, plasticizers and impact modifiers have flexural moduli and tensile strengths which are lower than the original polycarbonates. Other blends of polycarbonates containing so called antiplasticizers have easier melt flow and greater stiffness and strength as solids, but poor tensile strength, ductility and impact strength.

Illustrative examples of polycarbonate blends containing impact modifiers are disclosed in U.S. Pat. Nos. 4,438,231, 4,536,538 and 4,710,534. The first of these discloses multiphase composite interpolymer compositions comprising acrylate and methacrylate and an olefin-acrylate copolymer as an impact modifier. An alkali metal salt is present as a flame retardant. In the second, a combination of an amorphous polyester comprising units derived from 1,4-cyclohexane dimethanol and aromatic dicarboxylic acid or ester forming derivative and an olefin-acrylate copolymeric resin is disclosed as an impact modifier. In the third, a combination of an olefin diene copolymer and an acrylonitrile-butadiene-alkenylaromatic copolymer is disclosed as an impact modifier. Illustrative examples of experimental polycarbonate blends containing a tritolyl phosphate plasticizer are disclosed in a series of Journal articles. The three Journal articles are: A. Onu, R. Legras and J. P. Mercier, Journal of Polymer Science, Part A-2 Polymer Physics Edition v. 14, n. 7, Jul. 1976 p 1187-1199: R. Legras and J. P. Mercier, Journal of Polymer Science, Polymer Physics Edition, v. 15, n. 7, Jul. 1977, p. 1283-1289; R. Legras and J. P. Mercier, Journal of Polymer Science, Polymer Physics Edition, v. 17, n. 7, Jul. 1979, p. 1171-1181. An illustrative example of a polycarbonate blend containing a flame retardant is disclosed in U.S. Pat. No. 4,866,130. In this patent an aromatic sulfonic acid salt having a polyether side chain and an alkyl, halo, nitro, trihalomethyl or cyano substituent on the aromatic radical is disclosed as the flame retardant.

The present invention provides a class of plasticized polycarbonates which have a broad range of properties extending from flexural moduli and tensile strengths in excess of neat polycarbonate to low flexural modulus, low tensile strength materials. The high elastic modulus, high tensile strength materials are particularly useful in forming thin walled precision injection molded housings for electronic components. Thin walls and thin support webs can be easily formed because of low melt viscosity of the materials of the present invention. In addition to having a broad range of flexibilities and tensile strengths, the polycarbonate blends of the present invention are also flame retardant. The tendency of the blends to drip in the UL-94 test is expected to be eliminated by art recognized expedients such as the addition of polytetrafluoroethylene fibrils. The use of polytetrafluoroethylene to improve melt stability and flame retardancy is known in the art as exemplified by the teachings of U.S. Pat. No. 4,223,100.

In one of its aspects, the present invention comprises a matrix of a polycarbonate with a sufficient amount to lower the $T_g$ of the polycarbonate to a temperature below that of a corresponding neat polycarbonate of a diphosphate plasticizer (antiplasticizer) of the formula

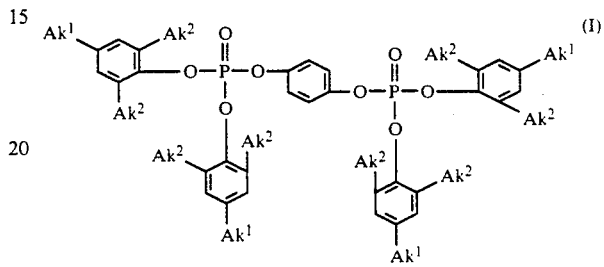

Wherein each $Ak^1$ is independently hydrogen or a methyl radical and each $Ak^2$ is independently a monovalent hydrocarbon radical having from one to four carbon atoms.

Preferably $Ak^1$ is hydrogen, and preferably each $Ak^2$ is methyl.

The polycarbonate-diphosphate matrix preferably contains from 70% to 99% by weight of the polycarbonate and from 1% to 30% by weight of the diphosphate plasticizer. More preferably the polycarbonate diphosphate matrix contains from 80% to 95% by weight of the polycarbonate and from 5% to 20% by weight of the diphosphate plasticizer.

If impact resistance rather than tensile strength is desired, an impact modifier can be added in an amount of from one to twenty parts by weight, based upon 100 parts by weight of any of the above plasticized polycarbonate matrices.

A preferred blend contains 75% to 95% by weight of polycarbonate, from 5% to 25% by weight of the diphosphate plasticizer and from five to ten parts by weight, based upon 100 parts by weight of the two component matrix, of an impact modifier. A preferred impact modifier is a butadiene-styrene-methyl methacrylate terpolymer. The impact modifier is preferably crosslinked to the degree that it is from 90% to 100% insoluble in acetone. The impact modifier preferably contains on a weight percentage basis from 60% to 70% butadiene, from 10% to 30% of methyl methacrylate and from 10% to 20% of styrene.

The polycarbonates which are components of this invention generally comprise structural units of the formula

wherein each $R^1$ is a divalent aliphatic, alicyclic or aromatic radical. The $R^1$ values may be different but are usually the same, and may be aliphatic, alicyclic, aromatic or mixed; those which are aliphatic or alicyclic generally contain up to about 8 carbon atoms. Suitable R¹ values include ethylene, propylene, trimethylene, tetramethylene, hexamethylene, dodecamethylene, poly1.4-(2-butenylene), poly-1,10-(2-ethyldecylene), 1,3-cyclopentylene, 1,3-cyclohexylene, 1,4-cyclohexylene, m-phenylene, p-phenylene, 4,4'-biphenylene, 2,2-bis(4-phenylene)propane, benzene-1,4-dimethylene (which is a vinylog of the ethylene radical and has similar properties) and similar radicals such as those which correspond to the dihydroxy compounds disclosed by name or formula (generic or specific) in U.S. Pat. No. 4,217,438, the disclosure of which is incorporated by reference herein. Also included are radicals containing non-hydrocarbon moieties. These may be substituents such as chloro, nitro, alkoxy and the like, and also linking radicals such as thio, sulfoxy, sulfone, ester, amide, ether and carbonyl. Most often, however, all R¹ radicals are hydrocarbon radicals.

Preferably at least about 60% and more preferably at least about 80% of the total number of R¹ values in the polycarbonate, and most desirably all of the R¹ values, are aromatic. The aromatic R¹ radicals preferably have the formula

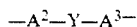

$$-A^2-Y-A^3-\qquad (III)$$

wherein each of $A^2$ and $A^3$ is a monocyclic divalent aromatic radical and Y is a bridging radical in which one or two atoms separate Az from $A^3$. The free valence bonds in formula III are usually in the meta or para positions of $A^2$ and $A^3$ in relation to Y. Frequent reference to bisphenols will be made hereinafter, but it should be understood that R¹ values derived from suitable compounds other than bisphenols may be employed as appropriate.

In formula III, the $A^2$ and $A^3$ values may be unsubstituted phenylene or substituted derivatives, illustrative substituents (one or more) being alkyl, alkenyl (e.g., crosslinkable-graftable moieties such as vinyl and allyl), halo (especially chloro and/or bromo), nitro, alkoxy and the like. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. It is most often a hydrocarbon radical and particularly a saturated radical such as methylene, cyclohexylmethylene, 2-[2.2.2]-bicycloheptylmethylene, ethylene, 2,2-propylene,1,1-(2,2-dimethylpropylene),1,1-cyclohexylene, 1,1-cyclopentdecylene, 1,1-cyclodecylene or 2,2especially a gem-alkylene radical. Also included, however, are unsaturated radicals and radicals which are entirely or partially composed of atoms other than carbon and hydrogen. Examples of such radicals are 2,2-dichloroethylidene, carbonyl, oxy, thio and sulfone. For reasons of availability and particular suitability for the purposes of this invention, the preferred radical of formula III is the 2,2-bis(4-4-phenylene)-propane radical, which is derived from bisphenol A and in which Y is isopropylidene and $A^2$ and $A^3$ are each p-phenylene.

The tetra(lower alkaryl) p-phenylene diphosphates which are used in the matrices of the present invention may be prepared by the following reaction sequence. The first step in the sequence comprises reacting a monohydroxyaromatic compound of the following formula

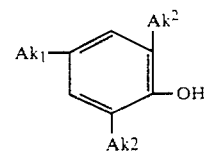

with phosphorus oxychloride (POCl₃) using an aluminum chloride catalyst (AlCl₃) to produce a chlorophosphoric acid diester of the formula

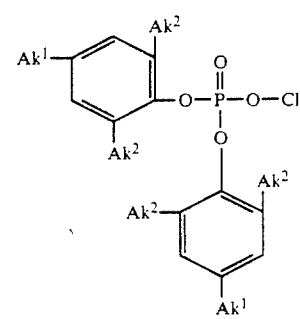

The diester is then reacted with hydroquinone, again using an aluminum chloride (AlCl₃) catalyst to produce the tetra(lower alkaryl) p-phenylene diphosphate of formula (I). The radicals present in and on the compounds int he above reaction sequence are all as defined above.

The tetraxylyl hydroquinone diphosphate of formula (VI) used in the following examples was made by the above procedure using the following reagents and reaction sequence.

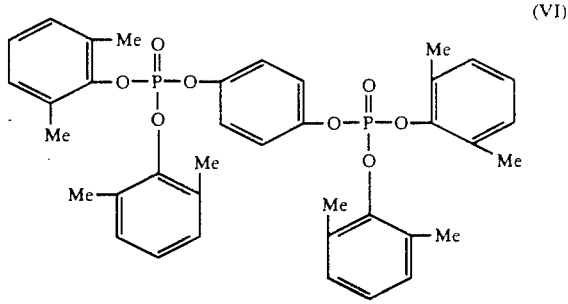

The first step in the sequence comprises reacting xylenol of the following formula

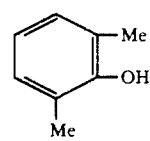

with phosphorus oxychloride (POCl₃) using an aluminum choride catalyst (AlCl₃) to produce a dixylyl monochloro phosphate ester of the formula

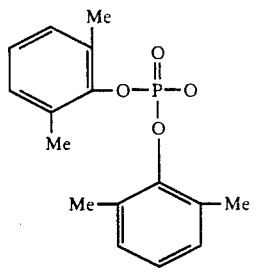
(VIII)

The diester is then reacted with hydroquinone of the formula,

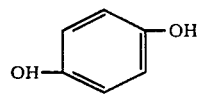
(IX)

again using an aluminum chloride (AlCl$_3$) catalyst to produce the tetraxylyl hydroquinone diphosphate of formula (VI).

While the addition of the tetra(lower alkaryl) p-phenylene diphosphate plasticizer to polycarbonate improved the flame retardance, melt flow, stiffness and strength of the blend, it may adversely affect the impact strength of the blend. To recover the impact resistance of the original polycarbonate, without losing the superior melt flow and flame retardance properties, an impact modifier may be added. Many materials which are known as impact modifiers for polycarbonate can be used, for example the impact modifiers disclosed in U.S. Pat. Nos. 4,438,231; 4,536,538; and 4,710,534 the disclosures of which are incorporated by reference. The disclosures are discussed briefly above.

The preferred impact modifier is Kanegafuchi ACE B56 terpolymer which contains on a weight percentage basis, 66% butadiene, 20% methyl methacrylate, and 14% styrene. The impact modifier is cross linked to the extent that it is 92% insoluble in acetone.

The preparation of the polycarbonate-tetra(lower alkaryl) p-phenylene diphosphate matrices and the addition of impact modifier to the matrices and the physical properties achieved thereby is shown below. All parts and percentages are on a weight basis unless otherwise indicated. The bisphenol-A (BPA) polycarbonate used was LEXAN ® 141 polycarbonate. LEXAN is a registered trademark of the General Electric Company. Tetraxylyl hydroquinone diphosphate was blended with the polycarbonate. The preparation of tetraxylyl hydroquinone diphosphate is described above. The impact modifier used was Kanegafuchi ACE B56 (B56) also described above.

Blends of BPA polycarbonate (PC) and tetraxylyl hydroquinone diphosphate plasticizer (TXHQDP) are transparent blends which exhibit reduced glass temperatures ($T_g$), reduced melt viscosities and yet greater flexural moduli and strengths than does neat PC. However, the incorporation of this plasticizer may reduce both the Dynatup impact strength and the notched Izod impact strength substantially.

To improve impact strength, matrices of PC, TXHQDP and an impact modifier, Kanegafuchi ACE B56, have been compounded on a twin screw extruder and injection molded. TXHQDP concentrations in the PC matrices were 10, 15 and 20 weight percent.

Each of these matrices was compounded with 3, 5 and 10 weight percent B56 impact modifier. The nine resulting blends were injection molded and characterized rheologically and mechanically. Flame resistance was also characterized. The resultant data as well as results of previous tests of PC/TXHQDP blends without impact modifier are set forth below.

I. PROPERTIES OF INJECTION MOLDINGS OF BLENDS WITHOUT IMPACT MODIFIER (all are Transparent and Colorless)

| A. Perkin Elmer Differential Scanning Calorimeter D.S.C. Glass Temperatures and Zero Shear Melt Viscosities $\eta$(at Temp., °C.) | | | | |
|---|---|---|---|---|
| Wt. % TXHQDP | $T_g$ (°C.) | $\eta$(200) (poise) X10 exp-6 | $\eta$(215) (poise) X10 exp-6 | $\eta$(225) (poise) X10 exp-6 |
| 0 | 148 | 1.3 | 0.55 | 0.15 |
| 5 | 135 | 0.5 | 0.15 | 0.070 |
| 10 | 120 | 0.18 | 0.060 | 0.030 |
| 15 | 110 | 0.065 | 0.030 | 0.017 |
| 20 | 101 | 0.03 | 0.013 | 0.0080 |
| 25 | 94 | 0.015 | 0.0080 | 0.0050 |
| 30 | 85 | — | — | — |

Thus 20% TXHQDP lowers $T_g$ to 101° C. and reduces the zero shear viscosities by factors of 20 to 40. At a frequency of 100 sec$^{-1}$ the blends are much more Newtonian; the reduction in viscosity from 0 to 20% plasticizer is only by factors of 5 to 10.

| | B. Mechanical Properties | | | | |
|---|---|---|---|---|---|
| Wt. % TXHQDP | Yield Strength (psi) | Ultimate Elongation (%) | Flex Modulus (ksi)* | Notched Izod Impact Strength (⅛") (ft-lbs/in) | Dynatup Impact Strength (ft-lbs) |
| 5 | 9200 | 170 | 320 | 1.4 | 57 |
| 10 | 9630 | 126 | 340 | 0.8 | 47 |
| 15 | 9970 | 121 | 410 | 0.6 | 46 |
| 20 | 10480 | 84 | 450 | 0.5 | 14 |
| 25 | 10490 | 146 | 460 | 0.3 | 1.5 |

Thus all blends are ductile in tensile tests, with moduli and yield stress equal to or greater than those of neat polycarbonate. Ductility as measured by the notched Izod test is decreased substantially by 5% or more TXHQDP but survives in the Dynatup test up to about 20% TXHQDP.

*ksi is the abbreviation for 1000 pounds per square inch.

| C. Flame Resistance: UL-94 Test | | | |
|---|---|---|---|
| Wt. % TXHQDP | Total FOT* (sec.) | Avg. FOT (sec.) | Bars Failing by Flaming Drips |
| 5  | 71.5 | 7.2 | #2, 3, 4 and 5 on second burns. |
| 10 | 20.8 | 2.1 | None — V-O** |
| 15 | 27.8 | 2.8 | #3 on second burn. |
| 20 | 21.3 | 2.1 | #5 on second burn. Note: #1, 2, 3 and 4 had melting material after flame out. |
| 25 | 10.9 | 1.1 | #2, 3, 4, 5 on second burns. #1 had melting material after flame-out. |

*Flame out time. Two burns on each bar.
**V-O indicates that flame out test was passed.
Based on FOT data alone the blends containing 10% or more TXHQDP would probably be V-O.

II. BLENDS OF PC RESIN/TXHQDP WITH KANEGAFUCHI ACE B56 IMPACT MODIFIER
(All are Opaque)

A. Mechanical Properties vs. TXHQDP and Impact Modifier content

| Matrix Composition (Total Wt. = 100 Parts) | Parts of Impact Modifier per 100 Parts Matrix | | |
|---|---|---|---|
| Wt. Resin/Wt. TXHQDP | 3 | 5 | 10 |
| 1. Flexural Moduli (ksi) | | | |
| 90/10 | 380 | 360 | 330 |
| 85/15 | 390 | 380 | 340 |
| 80/20 | 400 | 390 | 350 |

Thus all combinations above of TXHQDP and Impact Modifier result in modulus equal to or greater than that of neat polycarbonate.

| 2. Tensile Strengths (psi)/Ultimate Elongations (%) | | | |
|---|---|---|---|
| 90/10 | 9200/175 | 8850/198 | 8820/185 |
| 85/15 | 9450/175 | 9100/132 | 8350/138 |
| 80/20 | 9750/145 | 9350/151 | 8450/164 |

Thus, all of the above blends are ductile; high impact modifier contents reduce the yield stress below that of neat polycarbonate.

| 3. Impact Strength: Notched Izod (ft-lbs/in)//Dynatup (ft-lbs) (Specimen Thickness = 150 th in.) | | | |
|---|---|---|---|
| 90/10 | 2.9//50 | 14.6//48 | 13.4//43 |
| 85/15 | 1.2//45 | 12.9//46 | 13.8//45 |
| 80/20 | 0.8//49 | 1.1//47 | 12.5//45 |

Thus, all Dynatup failures are ductile, but ductility according to the Izod Impact test requires up to 5 parts of impact modifier at 15% TXHQDP and up to 10 parts of impact modifier at 20% TXHQDP.

B. Flame Resistance: UL-94 Test: Total FOT*/Average FOT/Footnote No.

| Matrix Composition (Total Wt. = 100 Parts) | Parts of Impact Modifier per 100 Parts Matrix | | |
|---|---|---|---|
| Wt. Resin/Wt. TXHQDP | 3 | 5 | 10 |
| 90/10 | 48.5/4.9/a | 40.1/5.0/b | 71.4/11.9/a |
| 85/15 | 18.7/1.9/d | 17.7/1.8/e | 76.8/7.7/f |
| 80/20 | 15.6/2.6/g | 6.1/1.0/h | 28.1/2.8/i |

*Flame-out time. Two burns on each bar.
Note: Failures due to flaming drips: Bar nos./Burn Nos.
a. Bars 1 & 2/2; b. Bars 3 & 4/2; c. Bars 1 & 3/2; d. V-O!!!; e. Bar 1/2 f. Bars 3,4 & 5/2; g. Bars 2/2 (also Bar 1/2 and Bar 3/2 melted after FOT); h. Bars 2 & 3/2 (Bar 1/2 melted after FOT); i. Almost V-O (Bar 3/2 failed due to flaming drip)
Based on FOT data alone all blends containing 15 and 20% TXHQDP would have been classed V-O.

MELT VISCOSITIES (POISE × $10^{-4}$) OF NEAT LEXAN ® 141 PC RESIN AND ITS BLENDS WITH TXHQDP AND KANEGAFUCHI ACE B56 IMPACT MODIFIER

| | Wt. % Impact Modifier | | | |
|---|---|---|---|---|
| | 0 | 3 | 5 | 10 |
| I. At 225° C. | | | | |
| A. At frequency = 0.1 rad/sec | | | | |
| Resin/TXHQDP (w/w) | | | | |
| 100/0 | 15.0 | | | |
| 90/10 | 3.0 | | 3.6 | |
| 85/15 | 1.7 | 1.8 | 2.0 | 3.6 |
| 80/20 | 0.80 | | 1.5 | |
| B. At frequency = 500 rad/sec (extrapolated from data to 250 rad/sec) | | | | |
| 100/0 | 2.3 | | | |
| 90/10 | 1.0 | | 2.0 | |
| 85/15 | .71 | 1.28 | 1.3 | 1.45 |
| 80/20 | .48 | | .86 | |

MELT VISCOSITIES (POISE × $10^{-4}$) OF NEAT LEXAN ® 141 PC RESIN AND ITS BLENDS WITH TXHQDP

| Resin/TXHQDP (w/w) | Melt Viscosity |
|---|---|
| II. At 215° C. | |
| A. At frequency = 0.1 rad/sec | |
| 100/0 | 55 |
| 90/10 | 6 |
| 85/15 | 2.9 |
| 80/20 | 1.3 |
| B. At frequency = 500 rad/sec (no extrapolation) | |
| 100/0 | 3.4 |
| 90/10 | 1.4 |

-continued

MELT VISCOSITIES (POISE × 10⁻⁴) OF NEAT LEXAN ® 141 PC RESIN AND ITS BLENDS WITH TXHQDP

| Resin/TXHQDP (w/w) | Melt Viscosity |
|---|---|
| 85/15 | 1.0 |
| 80/20 | .63 |

III. At 200° C.

PC RESIN/TXHQDP BLENDS HAVING KANEGAFUCHI ACE B56 IMPACT MODIFIER CONTENTS CRITICAL FOR DUCTILE IMPACT BEHAVIOR

| | $T_g$ °C. | | | | | | | |
|---|---|---|---|---|---|---|---|---|
| | 130° | | 120° | | 110° | | 100° | |
| | Dynatup Only | Dynatup & Izod | Dynatup Only | Dynatup & Izod | Dynatup Only | Dynatup & Izod | Dynatup Only | Dynatup & Izod |
| Wt. % TXHQDP in matrix | 7 | 7 | 10 | 10 | 15 | 15 | 20 | 20 |
| Parts B56/100 matrix | 0 | ~3 | 0 | 5 | 0 | 5 | ~3 | ~8 |
| $\eta_o^*/\eta_o^*$(PC) at 225° C. | .44 | .44* | .19 | .19* | .10 | .10* | .02* | .02* |
| Flex modulus (ksi) | ~355 | ~325 | ~365 | ~330 | 410 | 380 | 400 | 365 |
| Yield Stress (psi) | 9200 | ~8900 | 9600 | 8800 | 10,000 | 9100 | 9800 | 8400 |
| Ultimate Elongation (%) | 150 | 190 | 125 | 195 | 105 | 175 | 145 | 160 |
| Dynatup Strength (ft-lbs) | 45 | 50 | 45 | 48 | 46 | 47 | 35 | 45 |
| ⅛" Notched Izod (ft-lbs/in) | 0.7 | 14 | 0.7 | 14.5 | 0.6 | 13 | 0.2 | ~9 |

*Matrix Viscosities, ie, ratio of viscosities of blends with no impact modifier to viscosities of neat polycarbonate.

```
A. At frequency = 0.1 rad/sec
     100/0        130
     90/10         18
     85/15          6.5
     80/20          1.7
B. At frequency = 500 rad/sec
   (extrapolation from data
   to 250 rad/sec)
     100/0          3.9
     90/10          1.9
     85/15          1.3
     80/20          0.9
```

FLEXURAL MODULI (PSI × 10⁻³) OF NEAT LEXAN ® 141 PC RESIN AND ITS BLENDS WITH TXHQDP AND KANEGAFUCHI ACE B56 IMPACT MODIFIER

| | Wt. % Impact Modifier | | | |
|---|---|---|---|---|
| Resin/TXHQDP (w/w) | 0 | 3 | 5 | 10 |
| 100/0 | 340 | | | |
| 95/5 | 320 | | | |
| 90/10 | 340 | 380 | 360 | 330 |
| 85/15 | 410 | 390 | 380 | 340 |
| 80/20 | 450 | 400 | 390 | 350 |
| 75/25 | 460 | | | |

As is shown by the above, the addition of 20% TXHQDP to Lexan ® 140 resin reduces the blend $T_g$ to 100° C, and the melt viscosity by factors of 5 to 40 depending on temperature and shear rate. The flex modulus is raised by approximately a third and the tensile strength by roughly 15% However, the blend is brittle in the notched Izod test (though not the Dynatup test).

The addition of between 5 and 10 parts of impact modifier to 100 parts of the 80/20 blend restores its notched Izod impact toughness though reducing its modulus and yield stress to about the values associated with neat polycarbonate.

From the above data compositional requirements have been determined for eight blends that differ from each other in two respects, $T_g$ and toughness. First the amounts of TXHQDP necessary to reduce the matrix $T_g$ to 130, 120, 110 and 100° C. were determined. Second, the amounts of Kanegafuchi ACE B56 impact modifier just necessary to give a ductile, high-impact strength response in a) the Dynatup test and b) the notched Izod test at ambient temperature were defined for each of the four matrix compositions used to formulate the eight blends. The mechanical properties of each of these eight blends were then determined from graphs of each property vs. impact modifier content at each TXHQDP plasticizer level formulated. The properties of these eight blends are listed in the following table.

An examination of the profiles outlined in the above table and a comparison with the properties to prior art polycarbonate blends made "easy flow" by the addition of usual plasticizers of low $T_g$ shows that the blends disclosed here are superior in two respects. First the moduli and yield strengths of the blends of the present invention are greater than those for neat polycarbonate and much greater than those for polycarbonate having $T_g$ reduced by a conventional plasticizer and toughened with an impact modifier. Second, the blends of the present invention have higher flame resistance.

What is claimed is:

1. A plasticized polycarbonate composition comprising a matrix of an aromatic polycarbonate and a sufficient amount of tetra (2,6-xylyl) hydroquinone diphosphate to lower the Tg of the plasticized polycarbonate to a temperature below that of a corresponding neat polycarbonate.

2. The composition of claim 1 wherein the matrix contains form 70% to 99% by weight of the polycarbonate and from 1% to 30% by weight of the diphosphate plasticizer.

3. The composition of claim 1 wherein the matrix contains from 80% to 95% by weight of the polycarbonate and from 5% to 20% by weight of the diphosphate plasticizer.

4. The composition of claim 1 wherein the polycarbonate is a bisphenol A polycarbonate.

5. The composition of claim 1 containing an impact modifier in an amount of from one to twenty parts by weight, based upon 100 parts by weight of the polycarbonate-diphosphate plasticizer matrix.

6. The composition of claim 2 containing an impact modifier in an amount of from one to twenty parts by weight, based upon 100 parts by weight of the polycarbonate-diphosphate plasticizer matrix.

7. The composition of claim 3 containing an impact modifier in an amount of from one to twenty parts by weight, based upon 100 parts by weight of the polycarbonate-diphosphate plasticizer matrix.

8. The composition of claim 4 containing an impact modifier in an amount of from one to twenty parts by weight, based upon 100 parts by weight of the polycarbonate-diphosphate plasticizer matrix.

9. A composition comprising a matrix of 75-95% by weight of an aromatic polycarbonate and 5-25% by weight of tetra(2,6-xylyl) hydroquinone diphosphate and 5-10 parts by weight, per 100 parts of said matrix, of an impact modifier.

10. The composition of claim 9 wherein the impact modifier is a butadiene-styrene-methyl methacrylate terpolymer.

11. The composition of claim 10 wherein the impact modifier is crosslinked to the degree that it is from 90% to 100% insoluble in acetone.

12. The composition of claim 11 wherein the impact modifier contains on a weight percentage basis from 60% to 70% butadiene, from 10% to 30% of methyl methacrylate and from 10% to 20% of styrene.

13. The composition of claim 9 wherein the polycarbonate is a bisphenol A polycarbonate.

* * * * *